United States Patent [19]

Glazer

[11] Patent Number: 4,788,189

[45] Date of Patent: Nov. 29, 1988

[54] METHOD TO TREAT SMOKING WITHDRAWAL SYMPTOMS BY POTENTIATED CENTRAL NORADRENERGIC BLOCKING

[76] Inventor: Howard I. Glazer, 225 E. 64th St., Ste. 202A, New York, N.Y. 10021

[21] Appl. No.: 161,799

[22] Filed: Feb. 29, 1988

[51] Int. Cl.$^4$ ...................... A61K 31/24; A61K 31/54; A61K 31/415; A61K 31/495

[52] U.S. Cl. .................................. 514/221; 514/255; 514/401; 514/538; 514/540; 514/813

[58] Field of Search ............... 514/401, 813, 221, 255, 514/538, 540

[56] References Cited

U.S. PATENT DOCUMENTS 4,575,510  3/1986  Sjoerdsma ........................... 514/401
4,588,739  5/1986  Glassman ............................ 514/401

OTHER PUBLICATIONS

Chem. Abst. 106-97867f, (1987).

*Primary Examiner*—Stanley L. Friedman
*Assistant Examiner*—Stanley J. Friedman
*Attorney, Agent, or Firm*—Siegmar Silber

[57] ABSTRACT

Administering divided dose of oral Clonidine potentiated by an intramuscular tricyclic antidepressant alleviates the abstinence syndrome resulting from withdrawal of nicotine by smoking cessation. Patient response to the Clonidine/tricyclic serves as the basis for titrating the dosages of transdermal Clonidine and oral buspar administered daily for two weeks following the office visit. Behavioral counseling, supported by written and audio materials on diet, nutrition, exercise, stress management, and habit control, are provided to the patient. Following up support groups are also made available.

42 Claims, No Drawings

METHOD TO TREAT SMOKING WITHDRAWAL SYMPTOMS BY POTENTIATED CENTRAL NORADRENERGIC BLOCKING

FIELD OF THE INVENTION

This invention relates to a method of treating smoking withdrawal symptoms. More specifically the method includes assessing patient response to using an alpha 2 noradrenergic agonist by potentiating the alpha 2 noradrenergic agonist with a tricyclic antidepressant, and then after assessment, continuing treatment by using the alpha 2 noradrenergic agonist on a daily basis. The method further optionally employs the use of an anxiolytic substance, as required, during the initial smoking cessation period.

DISCLOSURE INFORMATION STATEMENT

In the discussion of cessation of cigarette smoking and the biochemical treatment of the withdrawal symptoms thereof, it is important to have some understanding of the pharmacodynamics of cigarette smoking, nicotine dependency, and craving reactions. The maintenance of habitual cigarette smoking serves the purpose of regulating anxiety and distress by producing a mild euphoria. Further, smoking avoids the tension and irritability of cigarette withdrawal. It is posited that the maintenance of cigarette smoking depends most on the intense craving for the drug (nicotine). Craving is defined by the preoccupation with, thoughts about or an urge for the habituating substance. According to Glassman et al in an article entitled, "Cigarette Craving, Smoking Withdrawal and Clonidine," Science, Vol. 226, p. 864-6 (Nov., 1984), craving for the tension-reducing drug nicotine develops in the absence of the drug because the habituated user experiences a rebound dysphoria and seeks the drug to eliminate that dysphoria.

In pharmacologic terms it has long been established that the action of nicotine on ganglia resembles that of acetylcholine in producing a strong initial stimulation of the receptor, but differs in that the resultant depolarization is greatly protracted. Thus paralysis of some duration is produced. During the brief stimulatory phase there may be nausea and increased intestinal activity, and a general constriction of arterioles and capillaries causing pallor, sweating, and increased blood pressure. The pharmacologic description as to the brief stimulatory phase is in concurrence with the romantic literary description of youngsters behind the barn enjoying (sic) their first encounter with cigarette smoking. During the paralytic phase the blood pressure falls and this effect adds to the impression of control through regulation of anxiety and distress. Here the cultural image, reinforced by cigarette advertisements of a smoker being a controlled, cool personality is also given credence by pharmacological studies of the effects of nicotine.

Nicotine also liberates catechol amines from the adrenal medulla and peripheral stores with a resultant sharp vasoconstriction accentuating the ganglionic effect. Acetylcholine is the transmitter at the ganglionic synapse, whether sympathetic or parasympathetic. After its release by the preganglionic ending it crosses to the receptor of the postganglionic fiber and causes depolarization of the membrane. This depolarization initiates an action potential in the postganglionic cell, which is propagated down the fiber. In the past, researchers have shown that acetylcholine also liberates norepinephrine in sympathetic ganglia, which then reduces transmission, acting as a "modulator" (Costa et al Science, 133:1822, 1961).

In treating the withdrawal symptoms of cigarette smoking, it is clear that both the biochemical/addiction factor and the psychosocial factor need to be addressed. Because of widespread acceptance of smoking, the treatment of smoking by the media, and the socially and legal status of smoking, many smokers find it difficult to understand the true magnitude of the risk associated with smoking. It is falsely assumed that, if cigarettes really posed a substantial health risk, more would be heard about the dangers of smoking. Although between 350,000 and 540,000 deaths per year in the U.S.A. are attributable to smoking (which translates into smoking being the cause of more deaths than all other drugs combined), an estimated 54 million Americans continue to smoke.

While some recognition of smoking hazards exists, the result has been a plethora of fad-like smoking cessation programs. Popular smoking cessation methods include "placebo cigarettes" devices to dilute cigarette smoke, satiation smoking, stop smoking groups, hypnosis and hypnotic tapes, psychotherapy, aversion therapy, and the use of nicotine administered through routes other than smoking. Smoking program quit rates average approximately 50%, but recidivism is high, with only approximately 15% remaining abstinent for one year.

While the biochemistry of nicotine habituation and of cigarette withdrawal is not completely understood, the theoretical basis for treatment is sufficiently established. The abstinence syndrome produced by withdrawal or addictive substances is associated with an abrupt increase in sympathetic outflow from the brain stem. In particular, noradrenergic neurons in the locus coeruleus (containing half of the noradrenergic neurons in the mammalian brain) show a marked increase in firing rate during withdrawal (Amaral and Sinnamon, 1978). It is also known that diminishing noradrenergic activity diminishes the acute phase of the withdrawal syndrome (Svensson, 1986). This suggests that central noradrenergic overactivity is a common feature in the pathophysiology of withdrawal syndromes seen in a variety of addictive substances.

In preparing for this application, a medical literature search for treatment of smoking withdrawal symptoms using alpha 2 noradrenergic agonists was conducted. The search revealed the Glassman et al, Science (1984) article, supra; W. S. Bond, "Psychiatric indications for clonidine; The neuropharmacologic and clinical basis," Journal of Clinical Psychopharmacology, Vol. 6, No. 2 (1986); and a K. I. Pearce, "Clonidine and smoking" [letter], Lancet (Oct. 4, 1986). None of these articles provided for the potentiation of clonidine using a tricyclic antidepressant or for the use of an anxiolytic substance therewith. No relevent patents were uncovered upon search.

SUMMARY OF THE INVENTION

By administering divided doses of oral clonidine hydrochloride potentiated by intramuscular amitriptyline hydrochloride, the effects of excessive noradrenergic sympathetic outflow from the brain stem caused by nicotine withdrawal is inhibited. This alleviates the withdrawal symptoms attributed to cessation of smoking. The oral administration of the clonidine and intramuscular administration of the amitriptyline match the peak plasma levels thus maximizing the potentiation. Amitriptyline is utilized due to its relative selectivity in blocking transport of norepinephrine, its short half-life, and its commercial availability in injectable form. Following the initial office visit of the clonidine/amitriptyline administrations the patient is maintained on clonidine and buspar for a period of two weeks. Buspar was selected for use as it provides the anxiolytic effects important in supporting addiction withdrawal, does not add to the sedative side effects of clonidine, and counteracts possible CNS side effects of clonidine including restlessness, anxiety, nervousness, insomnia, and vivid dreams. Clinical assessment of the patient reaction to the clonidine/amitriptyline administrations is used to titrate the maintenance dosages of clonidine and buspar.

DESCRIPTION OF THE PREFERRED EMBODIMENTS

The treatment of smoking withdrawal symptoms is provided by the method described hereinbelow and variations made possible through the optional steps. Basically, the biochemical reaction of smoking withdrawal is treated with an alpha-adrenergic agonist potentiated by a tricyclic antidepressant.

Alpha-adrenergic agonists are known to profoundly inhibit the release or norepinephrine. The inhibitory effect is mediated by alpha receptors pharmacologically distinct from classical alpha 1 receptors. These inhibitory receptors are designated alpha 2 and are located on presynaptic nerve terminals. These alpha 2 receptors mediate the presynaptic feedback inhibition of neural release of norepinephrine. Thus the activation of such alpha 2 receptors inhibits transmitter release. The net result of stimulating alpha 2 receptors is thus to produce a marked decrease in sympathetic outflow from the CNS.

Clonidine and lofexidine, a clonidine derivative, are selective alpha 2 noradrenergic agonists, clinically used as antihypertensives. By stimulating alpha 2 receptors, such substances produce a decrease in CNS sympathetic outflow. The site at which this effect is exerted appears to be in the lower brain stem region, an area rich in cell bodies and nerve terminals containing norepinephrine. In the description which follows, in the belief that members of the class of selective alpha 2 noradrenergic agonists act in the same manner, clonidine and its derivative lofexidine are collectively referrred to as "clonidine." Clonidine is rapidly and almost completely absorbed after oral administration, showing peak plasma concentrations in 1 to 3 hours and easily penetrates into the CNS. Plasma half-life of clonidine averages 9 hours. Clonidine is described in Zeile et al, U.S. Pat. No. 3,202,660 assigned to C. H. Boechringer Sohn, Ingelheim am Rheim, West Germany, issued 1965, and lofexidine is described in H. Baganz et al, U.S. Pat. No. 3,966,757 assigned to Nordmark-Werhe GmbH, Hamburg, West Germany, issued 1976.

Tricyclic antidepressants presently consist of a class of nine chemically related analog compounds derived from imipramine. Included in this class are imipramine, desipramine, amitriptyline, nortriptyline, doxepin, protriptyline, trimipramine, maprotiline and amoxapin. Typical of the group is amitriptyline, which is described in Tristam et al, U.S. Pat. No. 3,205,264 assigned to Merck & Co., Rahway, N.J., issued 1965. Tricyclic antidepressants vary in their potency and monoamine selectivity but all share the ability to produce an immediate reduction in firing rate of neurons containing norepinephrine. While not completely understood, this is believed to be a consequence of blockade of monoamine uptake with a resultant increase in their action upon presynaptic autoreceptors (including alpha 2 adrenergic receptors) that regulate transmitter release from monoaminergic neurons. Tricyclic antidepressants show only moderate (48%±11%) availability from oral administration with plasma concentrations peaking in 2 to 8 hours. Inactivation of tricyclic antidepressants vary considerably with half lives ranging from 16 hours for amitriptyline to 80 hours for protriptyline.

Thus tricyclic antidepressants act synergistically to potentiate the action of clonidine. Clonidine stimulates the alpha 2 noradrenergic presnyaptic receptors which inhibit neuronal release of noreipinephrine, reducing the firing rate of the noradrenergic neurons. Tricyclic antidepressants inhibit neuronal transport (blocking reuptake) of norepinephrine, further stimulating alpha 2 receptors, potentiating the effects of Clonidine in reducing CNS sympathetic outflow from the brain stem.

As an optional part of the treatment, an anxiolytic substance is used, as required in conjunction with the clonidine during the daily treatment portion. These substances include meprabamates, benzodiazepines, and azospirodecanediones - the latter being a new group. Buspirone (Buspar$^R$) is currently the only representative of a new class of anxiolytics, the azospirodecanediones. Buspirone is pharmacologically distinct from the benzodiazephines, does not influence the binding of benzodiazepines, or GABA, lacks anticonvulsant activity, and shows minimal interaction with CNS depressants. Clinical data suggests that Buspirone is an effective antianxiety agent producing distinctly less sedation that benzodiazepines.

Before receiving the adrenergic blocking treatment, patients complete an extensive medical/psychological/smoking history questionnaire. Patients then participate in a psychoeducational seminar of approximately one hour duration. The seminar explains the pharmacological basis of the treatment and provides smoking-cessation related information on weight gain, diet, nutrition, exercise, stress management and habit control. Additionally printed materials describing the smoking cessation program, an audio cassette tape with hypnotic-type relaxation exercises, and a biofeedback device measuring peripheral vascular flow are provided to each patient. A medical history review is conducted with particular emphasis on contraindications to use of clonidine including coronary insufficiency, recent myocardial infarction, cerebral vascular disease, chronic renal failure, or retinal degeneration, and contraindications to use of amitriptyline including a history of seizures, urinary retention, acute-angle glaucoma, intraocular pressure, or cardiovascular disease. A routine medical examination is conducted including 12-lead resting electrocardiogram, urinalysis, complete blood count, serum electrolytes and SMA-4 panel, and chest x-ray. Patients with medical contraindications are excluded from treatment.

In accord with the method of the present invention, patients who from medical history and examination findings are suitable candidates for the potentiated noradrenergic block first receive as part of the assessment procedure an intramuscular injection of one (1) milliliter of sterile solution containing 10 mg of amitriptyline hydrochloride, 44 mg of dextrose, 1 ml of water for injection, and as preservatives, 1.5 mg of methylparaben, and 0.2 mg of propylparaben. Further and also as part of the assessment procedure, immediately following this injection the patient receives 0.1 mg of clonidine hydrochloride orally. This may be administered either in tablet form or dissolved in water. By this procedure which constitutes the administration of a partial dose of the potentiated noradrenergic block, the patient sensitivity to this drug combination, and the dosages to be used in the subsequent administration of the potentiated noradrenergic block are determined. Approximately 30 to 45 minutes after the initial clonidine/amitriptyline administration, patients are observed for drug reactions, including: drowsiness and sedation, agitation and restlessness, dizziness, dryness of the mouth eyes and nasal mucosa, nausea, motor incoordination, and significant blood pressure changes, particularly orthostatic hypotention. Patients who do not exhibit any of these symptoms to excess, both by clinical observation and self-report receive a second potentiated noradrenergic block. Patients showing a strong response to the initial potentiated drug administration are not given a second potentiated administration, but are placed directly onto the daily treatment dosage of maintenance medications. Accordingly, if the patient seems particularly responsive to either the clonidine or the amitriptyline, the patient may receive a second assessment dosage of the other. More typically, for those continuing to the second potentiated drug administration the initial procedure is repeated with the patient receiving 10 mg of amitriptyline hydrochloride by intramuscular injection followed immediately by 0.1 mg of clonidine hydrochloride orally either as a tablet or dissolved in water. After an additional period of 30 to 45 minutes the patients are again observed to further assess sensitivity to the clonidine/amitriptyline combination. Clinical observations are made and self-reports solicited on the same symptoms monitored after the initial potentiated drug administration.

On days 2 through 13 the patient takes the prescribed alpha adrenergic agonist, clonidine hydrochloride in a timed delivery, namely, a transdermal therapeutic system (TTS) referred to as clonidine HCL and the transdermal patch as clonidine HCL-TTS. The TTS patch is placed on the upper part of the chest area. Clonidine HCL-TTS comes in three strengths (0.1, 0.2, and 0.3 mg per day) designated respectively as TTS-1, TTS-2, and TTS-3. The patient's response to the clonidine/amitriptyline administrations determines which strength to use. Patients not given the second potentiated drug administration or those showing significant side effects to the second administrations are given the TTS-1. TTS-2 is most commonly used and is given to those showing a moderate reaction to the potentiated drug administrations. A patient responding with little or no objectively observable or self-reported side effects is given the TTS-3. In the specific protocol at hand, two successive transdermal patches are used -- the first one for seven days and the second one for five days. One 0.1 mg. clonidine tablet is taken on each of days 14 and 15 regardless of the strength of the clonidine patch used. Concomitant with the use of the clonidine patch (i.e. days 2 through 13) the patient takes as required, an anxiolytic substance, preferably from the meprobamates, azospirodecanediones or benzodiazepanes. Here, the choice within the protocol is buspirone or Buspar$_R$ (5mg) up to four times a day as needed for agitation, restless, or anxiety, and on days 14 and 15 no more than two 5 mg Buspar tablets are taken.

Typically following the in office administration of the noradrenergic block, a patient reports feeling some lightheadedness, drowsiness, motor incoordination, and dryness. These effects usually dissipate within twelve hours. However, it has been estimated that up to 10% of patients are intolerant of clonidine and will continue to experience sedation, dizziness, and mild nausea. Similarly, prevalence rates of significant side effects to amitriptyline run as high as 5%. These include epigastric distress, dizziness, tachycardia, blurred vision, and palpitations. Since the amitriptyline is administered only during the office visit, however, the side effects thereof are of only limited duration. Patients are informed, following the office visit that they should drink no alcohol, take no medications that act snynergistically with the potentiated adrenergic block, and that this medication may impair mental and physical abilities required for the performance of hazardous tasks, such as operating machinery or driving a motor vehicle. patients who report persistant sedation or drowsiness first have the Buspar tablets reduced or eliminated, and, if necessary, the clonidine doage level is reduced until symptoms are tolerable.

Since withdrawal symptoms in response to smoking cessation are most pronounced in the first 24 hours, producing an immediate and profound inhibition of release of norepinephrine and a marked decrease in sympathetic outflow from the brain stem produces a dramatic reduction of smoking withdrawal symptoms. The follow up treatment maintains the noradrenergic blocking by clonidine for the subsequent two weeks. Even though nicotine is eliminated from the system is approximately 72 hours, withdrawal symptoms may go on for as long as two weeks. The restlessness and agitation that often accompany withdrawal are significantly reduced by the buspar.

Individuals who wished to stop smoking were recruited for clinical trials through private referral networks. Smokers were categorized by age, sex, number of cigarettes smoked daily, number of years smoking, nicotine content of cigarettes, and self rating of strength of desire to quit. During the course of the clinical trials patients were treated with clonidine alone, intramuscular amitriptyline alone, clonidine potentiated with a variety or orally administered tricyclic antidepressants or clonidine potentiated with intramuscular amitriptyline. While the mechanism is not complete understood, it is believed that during smoking cessation, the withdrawal symptoms upon treatment by the protocol of this invention are ameliorated by the attenuation of the release of norepinephrine. This occurs as the result of the alpha 2 agonistic action of the assessment treatment of clonidine potentiated by amitriptyline and the maintenance treatment of clonidine.

Supporting this view are the clinical studies related to the hereinabove protocol. These consisted initially of a within-subject design wherein the patients' urges to smoke or cravings were measured by self-report ratings. Oral clonidine produced an average reduction of craving of 68%; intramuscular amitriptyline produced an average of 28% reduction; oral clonidine with oral tricylcic antidepressants produced an average of 78% reduction; and, oral clonidine with intramuscular amitriptyline produced an average of 89% reduction of self-rated urge to smoke. Further clinical trials with smoking cessation patients clearly indicated that dividing the administration of the clonidine/amitriptyline provided a more refined technique for assessment of patient sensitivity of this drug combination, thus allowing more accurate determination of the optimal maintenance dose of clonidine. For patients experiencing restlessness, agitation, or anxiety, Buspirone was found to be as effective as the benzodiazepines without accentuating drowsiness or sedation produced by the clonidine.

The method for treating cigarette smoking withdrawal is thus seen from the previous discussion to comprise the following steps:

a. orally administering to said patient, under observable conditions, a predetermined assessment dosage of clonidine hydrochloride as an alpha 2 noradrenergic agonist;

b. simultaneously with step a., hereinabove, administering a dosage of amitriptyline hydrochloride to potentiate the blocking effect of the clonidine, said step further comprising the substeps of:

(1) preparing an injectible sterile solution of the amitriptyline hydrochloride in water with dextrose and preservatives;

(2) injecting the solution, described in substep It has been clearly shown from data collected using the above method that smoking withdrawal symptoms are successfully treated with clonidine, an assessment treatment utilizing clonidine hydrochloride as potentiated by amitriptyline hydrochloride which assessment dosage is followed by daily treatment doeses of clonidine hydrochloride with optional concomitant daily treatment of buspirone. b. (1) above, intramuscularly into the patient;

c. assessing the potentiated clonidine application by monitoring patient response thereto, said step further comprising the substeps of:

(1) repeating the assessment dosage of clonidine hydrochloride as described in step a., hereinabove;

(2) continually monitoring the patient response to determine the affect of the blocking agent; and, d. administering during the next successive smoking cessation period a daily treatment of clonidine hydrochloride as determined by aforesaid assessment; and, e. simultaneously with step d., hereinabove, administering successive daily treatment dosages of buspirone; to thereby relieve withdrawal symptoms.

Although the best mode of the invention has been described herein in some detail, it has not been possible to include each and every variation. Those skilled in the art of the treatment of smoking withdrawal will be able to make slight variations in the arrangement suggested hereby without departing from the spirit of the invention and still be within the scope of the claims appended hereto.

What is claimed is:

1. A method for treating cigarette smoking withdrawal symptoms of a nicotine-habituated patient comprising the following steps:

a. administering to said patient, a predetermined initial dosage of clonidine hydrochloride;

b. simultaneously with step a., hereinabove, administering a imipramine derivative to potentiate the blocking effect of the clonidine hydrochloride;

c. administering during the initial smoking cessation period successive daily treatment dosages of clonidine hydrochloride;

d. simultaneously with step c., hereinabove, for relief of withdrawal symptoms administering successive daily treatment dosages of one of a specific subclass of anxiolytic substances selected from the group consisting of benzodiazepines, azospirodecanediones, and meprobamates.

whereby the withdrawal symptoms experienced upon cessation of smoking are relieved.

2. A method as described in claim 1, wherein said initial dosage is 0.1 mg dosage of clonidine hydrochloride said dosage being orally administered.

3. A method as described in claim 2, wherein the tricyclic antidepressant is an imipramine derivative selected from the group consisting of imipramine, desipramine, amitriptyline, nortriptyline, doxepin, protriptyline, trimipramine, maprotiline, and amoxapin.

4. A method as described in claim 3 wherein said imipramine derivative is amitriptyline.

5. A method as descried in claim 4, wherein for potentiation, 10 mg. dosage of amitriptyline hydrochloride is injected intramuscularly.

6. A method as described in claim 5, wherein said initial dosage is repeated until a maximum total dosage of up to 0.3 mg. of clonidine hydrochloride is orally administered.

7. A method as described in claim 6, wherein simultaneously with the repetition of the initial dosage, said potentiation dosage is repeated, as required until a maximum total dosage of up to 30 mg. of amitriptyline hydrochloride is injected intramuscularly.

8. A method as described in claim 5, wherein said potentiation dosage is repeated until a maximum total dosage of up to 30 mg. of amitriptyline hydrochloride is injected intramuscularly.

9. A method as described in claim 8, wherein simultaneously with the repetition of the potentiation dosage, said initial dosage is repeated, as required, until a maximum total dosage of up to 0.3 mg. of clonidine hydrochloride is orally administered.

10. A method as described in claim 5, wherein the daily treatment dosage is continued for 14 days next succeeding the day on which the initial dosage is administered.

11. A method as described in claim 5, wherein step c. is a timed delivery form of clonidine hydrochloride.

12. A method as described in claim 11, wherein the timed delivery form is a transdermal therapeutic system.

13. A method as described in claim 12, wherein the daily treatment dosage of clonidine is selected from a group consisting of 0.1 mg. clonidine hydrochloride, 0.2 mg. clonidine hydrochloride, and 0.3 mg. clonidine hydrochloride.

14. A method for treating cigarette smoking withdrawal nicotine-habituated patient comprising the following steps:

a. administering to said patient a predetermined initial dosage of clonidine;

b. simultaneously with step a., hereinabove, administering an imipramine derivative to potentiate the blocking effect of the clonidine, said step further comprising the substeps of:

(1) preparing an injectible sterile solution of the imipramine derivative in water with dextrose and preservatives;

(2) injecting the solution, described in substep b.(1) above, intramuscularly into the patient;

c. repeating the initial dosage of clonidine as described in step a., hereinabove;

d. administering during the next successive smoking cessation period a daily treatment dosage of clonidine; and, e. simultaneously with step d., hereinabove, for relief of withdrawal symptoms administering successive daily treatment dosages of an one of a specific subclass of anxiolytic substances selected from the group consisting of benzodiazepines, azospirodecanediones, and meprobamates.

whereby the withdrawal symptoms experienced upon cessation of smoking are relieved.

15. A method as described in claim 1, wherein said one of a specific subclass of anxiolytic substances of step d. is a daily treatment dosage of an azospirodecanediones.

16. A method as described in claim 15, wherein said azospirodecanediones is buspirone and the daily treatment dosage is, as required, up to a maximum total dosage of 20 mg.

17. A method as described in claim 14, wherein said initial dosage is 0.1 mg dosage of clonidine hydrochloride, said dosage being orally administered.

18. A method as described in claim 17 wherein said imipramine derivative is selected from the group consisting of imipramine, desipramine, amitriptyline, nortriptyline, doxepin, protriptyline, trimipramine, maprotiline, and amoxapin.

19. A method as described in claim 18 wherein said imipramine derivative is amitriptyline.

20. A method as described in claim 19, wherein said injectible solution comprises 10 mg of amitriptyline hydrochloride, 44 mg. of dextrose, 1.5 mg. of methylparaben, and 0.2 mg. of propylparaben in 1 ml. of water.

21. A method as described in claim 20 wherein said initial dosage is repeated until a maximum total dosage of up to 0.3 mg. of clonidine hydrochloride is orally administered.

22. A method as described in claim 21, wherein, simultaneously with the repetition of the initial dosage, said potentation dosage is repeated, as required until a maximum total dosage of up to 30 mg. of amitriptyline hydrochloride is injected intramuscularly.

23. A method as described in claim 20, wherein said potentiation dosage is repeated until a maximum total dosage of up to 30 mg. of amitriptyline hydrochloride is injected intramuscularly.

24. A method as described in claim 23, wherein simultaneously with the repetition of the potentiation dosage, said initial dosage is repeated, as required, until a maximum total dosage of up to 0.3 mg. of clonidine hydrochloride is orally administered.

25. A method as described in claim 20, wherein said daily treatment dosage of step d. is a timed delivery form of clonidine hydrochloride.

26. A method as described in claim 25, wherein the timed delivery form is a transdermal therapeutic system.

27. A method as described in claim 20, wherein the daily treatment dosage of clonidine is selected from a group consisting of 0.1 mg. clonidine hydrochloride, 0.2 mg. clonidine hydrochloride, and 0.3 mg. clonidine hydrochloride.

28. A method as described in claim 27, wherein the daily treatment dosage is continued for 14 days next succeeding the day on which the assessment dosage is adminsitered.

29. A method as described in claim 14, wherein said one of a specific subclass of anxiolytic substances of step e. is a daily treatment dosage of an azospirodecanediones.

30. A method as described in claim 29 wherein said azospirodecanediones is buspirone and the daily treatment dosage is, as required, up to a maximum total dosage of 20 mg.

31. A method for treating cigarette smoking withdrawal symptoms of a nicotine-habituated patient comprising the following steps:
a. orally administering to said patient, a predetermined initial dosage of clonidine hydrochloride;
b. simultaneously with step a., hereinabove, administering a dosage of amitriptyline hydrochloride to potentiate the blocking effect of the clonidine, said step further comprising the substeps of:
   (1) preparing an injectible sterile solution of the amitriptyline hydrochloride in water with dextrose and preservatives;
   (2) injecting the solution, described in substep b.(1) above, intramuscularly into the patient;
c. repeating the initial dosage of clonidine hydrochloride as described in step a., hereinabove;
d. administering during the next successive smoking cessation period a daily treatment dosage clonidine hydrochloride; and,
e. simultaneously with step d., hereinabove, administering successive daily treatment dosages of buspirone; to thereby relieve withdrawal symptoms; and, whereby the withdrawal symptoms experienced upon cessation of smoking are relieved.

32. A method as described in claim 31, wherein said step a. assessment dosage is a 0.1 mg dosage of clonidine hydrochloride administered orally.

33. A method as described in claim 32, wherein step b. is said injectible solution comprises 10 mg. of amitriptyline hydrochloride, 44 mg. of dextrose, 1.5 mg. of methylparaben, and 0.2 mg. of propylparaben in 1 ml. of water.

34. A method as described in claim 33, wherein said initial dosage is repeated until a maximum total dosage of up to a 0.3 mg of clonidine hydrochloride is orally administered.

35. A method as described in claim 34, wherein simultaneously with the repetition of the initial dosage, said potentiation dosage is repeated, as required until a maximum total dosage of up to 30 mg. of amitriptyline hydrochloride is injected intramuscularly.

36. A method as described in claim 33, wherein said potentiation dosage is repeated until a maximum total dosage of up to 30 mg. of amitriptyline hydrochloride is injected intramuscularly.

37. A method as described in claim 36, wherein simultaneously with the repetition of the potentiation dosage, said initial dosage is repeated, as required, until a maximum total dosage of up to 0.3 mg. of clonidine hydrochloride is orally administered.

38. A method as described in claim 33, wherein said daily treatment dosage of step d. is a timed delivery form of clonidine hydrochloride.

39. A method as described in claim 38, wherein the timed delivery form is a transdermal therapeutic system.

40. A method as described in claim 33, wherein the daily treatment dosage of clonidine is selected from a group consisting of 0.1 mg. clonidine hydrochloride, 0.2 mg. clonidine hydrochloride, and 0.3 mg. clonidine hydrochloride based on observed response of the patient to said assessment dosage.

41. A method of described in claim 40, wherein the daily treatment dosage is continued for 14 days next succeeding the day on which the assessment dosage is administered.

42. A method as described in claim 31 wherein said daily treatment dosage of buspirone is, as required, up to a maximum total dosage of 20 mg.

* * * * *